United States Patent
Luh et al.

(10) Patent No.: US 7,128,983 B2
(45) Date of Patent: Oct. 31, 2006

(54) FURAN-CONTAINING HOLE TRANSPORTING MATERIALS

(75) Inventors: Tien-yau Luh, Taipei (TW); Lingzhi Zhang, Guangdong (CN); Chin-Fa Lee, Kinmen (TW); Chung-Chih Wu, Taipei (TW); Cheih-Wei Chen, Taichung County (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 10/643,041

(22) Filed: Aug. 18, 2003

(65) Prior Publication Data

US 2004/0131883 A1 Jul. 8, 2004

Related U.S. Application Data

(60) Provisional application No. 60/404,090, filed on Aug. 16, 2002.

(51) Int. Cl.
*H05B 33/12* (2006.01)
*C07D 307/02* (2006.01)
*H01L 27/32* (2006.01)
*H01L 51/50* (2006.01)

(52) U.S. Cl. ............ 428/690; 428/917; 313/504; 313/506; 549/472; 549/505; 549/507

(58) Field of Classification Search .......... 428/690, 428/917; 313/504, 506; 549/472, 505, 507
See application file for complete search history.

(56) References Cited

U.S. PATENT DOCUMENTS 5,281,489 A * 1/1994 Mori et al. ............ 428/690
5,563,424 A * 10/1996 Yang et al. ............ 257/40
2003/0091860 A1 * 5/2003 Oshiyama et al. ......... 428/690

FOREIGN PATENT DOCUMENTS

JP 07-325329 A * 12/1995

OTHER PUBLICATIONS

Parakka et al., Synthetic Metals, 68, (1995), pp. 275-279.*
Hucke et al., J. Org. Chem. (1998), 63, p. 7413-7417.*
Bilik et al., Chembiochem, (2001), vol. 2, pp. 559-569.*
Adachi et al., Appl. Phys. Lett., 56 (9), Feb. 26, 1990, p. 799-801.*
Chemical and Pharmaceutical Bulletin, 29(3), (1981), p. 635-645.*
Lee et al., "One-Pot Synthesis of Substituted Furans and Pyrroles from Propargylic Dithioacetals, New Annulation Route to Highly Photoluminescent Oligoaryls", J. Am. Chem. Soc., 122:4992-4993, 2000.
Zhang et al., "Non-amine-based furan-containing oligoaryls as efficient hole transporting materials", Chem. Commun., 2336-2337, 2002.

* cited by examiner

*Primary Examiner*—Dawn L. Garrett
(74) *Attorney, Agent, or Firm*—Fish & Richardson P.C.

(57) ABSTRACT

A furan-containing compound of formula (I):

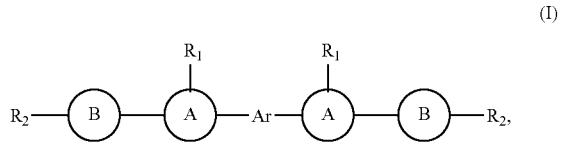

(I)

Ar is aryl, heteroaryl, or oligoaryl; A is furyl; B is aryl or heteroaryl; $R_1$ is hydrogen, alkenyl, alkynyl, aryl, heteroaryl, cyclyl, heterocyclyl, or oligoaryl; and $R_2$ is hydrogen, alkyl, alkenyl, alkynyl, aryl, heteroaryl, cyclyl, or heterocyclyl. The compound is useful as a hole transporting material in an organic light emitting diode device.

38 Claims, No Drawings

FURAN-CONTAINING HOLE TRANSPORTING MATERIALS

CROSS REFERENCE TO RELATED APPLICATION

This application claims priority to U.S. Provisional Application Ser. No. 60/404,090, filed on Aug. 16, 2002, the contents of which are incorporated herein by reference.

BACKGROUND

Organic light emitting diodes (OLEDs) can be used in a wide range of lightings, as well as high and low resolution display applications. The simplest OLED device contains an organic emission layer sandwiched between two electrodes that inject electrons and holes. The electrons and holes meet in the organic emission layer and produce light. Insertion of electron or hole transporting layers between the two electrodes renders the light production more efficient. See, e.g., Tang et al. (1987) *Applied Physics Letters* 51: 913–915, Burroughs et al. (1990) *Nature* 347: 539; Adachi et al. (1988) *Japanese Journal of Applied Physics* 27: L269–L271, and Mitschke and Bäuerle (2000) *J. Mater. Chem.* 10: 1471–1507.

SUMMARY

This invention relates to compounds useful as a hole transporting material in an OLED device.

In one aspect, this invention features a furan-containing compound of formula (I):

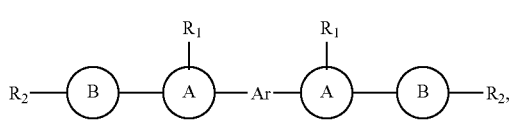

(I)

Ar is aryl, heteroaryl, or oligoaryl; A is a furyl ring; B is an aryl or heteroaryl ring; $R_1$ is hydrogen, alkenyl, alkynyl, aryl, heteroaryl, cyclyl, heterocyclyl, or oligoaryl; and $R_2$ is hydrogen, alkyl, alkenyl, alkynyl, aryl, heteroaryl, cyclyl, or heterocyclyl. Note that the two A groups, as well as the two B groups, the two $R_1$ groups, and the two $R_2$ groups can be the same or different. Further, each $R_1$ and each $R_2$ are bonded to any suitable positions on rings A or B.

A subset of the compounds encompassed by the above formula is featured by that A is furyl substituted at positions 2 and 5. Another subset is featured by that B is aryl (e.g., phenyl). In these compounds, $R_2$ can be hydrogen. A further subset is featured by that Ar is aryl (e.g., phenyl) or oligoaryl (e.g., biphenyl). In these compounds, A can be furyl substituted at positions 2 and 5, B can be aryl (e.g., phenyl), $R_1$ can be phenyl, optionally substituted at position 3 of furyl, and $R_2$ can be hydrogen.

Alkyl, alkenyl, aryl, heteroaryl, oligoaryl, cyclyl, or heterocyclyl mentioned above refers to both substituted and unsubstituted moieties. The term "substituted," in turn, refers to one or more substituents (which may be the same or different), each replacing a hydrogen atom. Examples of substituents include halogen, amino, alkylamino, arylamino, dialkylamino, alkyl-arylamino, diarylamino, hydroxyl, mercapto, cyano, nitro, trialkyl silyl, $C_1$–$C_6$ alkyl, $C_1$–$C_6$ alkenyl, $C_1$–$C_6$ alkoxy, aryl, heteroaryl, cyclyl, or heterocyclyl, wherein alkyl, alkenyl, alkoxy, aryl, heteroaryl, cyclyl, and heterocyclyl are optionally substituted with $C_1$–$C_6$ alkyl, halogen, amino, alkylamino, arylamino, dialkylamino, diarylamino, hydroxyl, mercapto, cyano, or nitro.

In some embodiments, the substituents are halogen, cyano, dialkylamino, alkyl-arylamino, diarylamino, alkyl, fluoroalkyl, trialkyl silyl, aryl, alkenyl, alkoxy, or a combination thereof.

As used herein, alkyl includes both linear and branched alkyl groups containing 1 to 6 carbon atoms. The term "alkenyl" refers to linear or branched alkenyl groups containing 2 to 6 carbon atoms. The term "aryl" refers to a hydrocarbon ring system having at least one aromatic ring. Examples of aryl moieties include, but are not limited to, phenyl, naphthyl, and pyrenyl. The term "heteroaryl" refers to a hydrocarbon ring system having at least one aromatic ring which contains at least one heteroatom such as O, N, or S. Examples of heteroaryl moieties include, but are not limited to, pyridinyl, carbazolyl, and indolyl. The term "oligoaryl" refers to a moiety containing 2 to 5 aryl or heteroaryl groups bridged by covalent bonds. Examples of oligoaryl include, but are not limited to, biphenyl. The terms "cyclyl" and "heterocyclyl" refer to partially and fully saturated mono-, bi-, or tri-cyclic rings having from 4 to 14 ring atoms. A heterocyclyl ring contains one or more heteroatoms (e.g., O, N, or S). Exemplary cyclyl and heterocyclyl rings include cycylohexane, piperidine, piperazine, morpholine, thiomorpholine, and 1,4-oxazepane.

In another aspect, this invention features an electro-luminescence device that includes an anode layer, a hole transporting layer, an electron transporting layer, and a cathode layer. In this device, the anode layer, the hole transporting layer, the electron transporting layer, and the cathode layer are disposed in the above order. The hole transporting layer includes a furan-containing compound of formula (I), in which Ar is aryl, heteroaryl, or oligoaryl; A is furyl; B is aryl or heteroaryl; $R_1$ is hydrogen, alkyl, alkenyl, alkynyl, aryl, heteroaryl, cyclyl, heterocyclyl, or oligoaryl; and $R_2$ is hydrogen, alkyl, alkenyl, alkynyl, aryl, heteroaryl, cyclyl, or heterocyclyl.

Shown below are exemplary compounds that can be used in the electro-luminescence device described above:

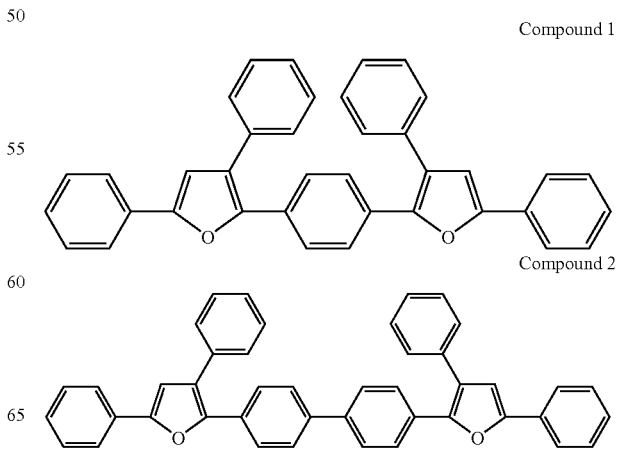

Compound 1

Compound 2

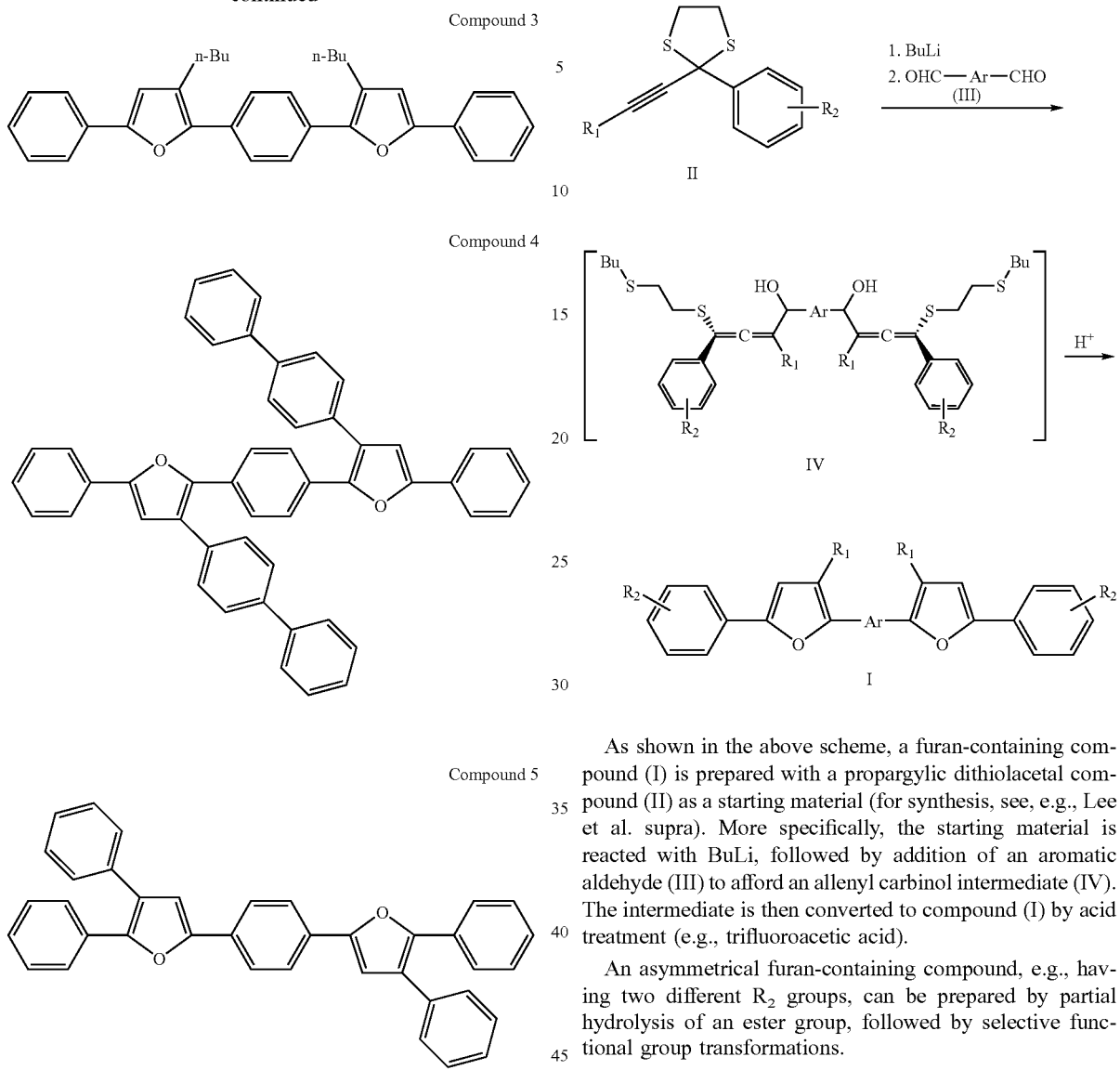

Other features, objects, and advantages of the invention will be apparent from the description and from the claims.

DETAILED DESCRIPTION

This invention relates to furan-containing compounds and their use as a hole transporting material in an electroluminescence device.

The furan-containing compounds described in Summary can be prepared by methods well known to a skilled person in the art. See, e.g., Pelter et al. (1997) *Tetrahedron* 53: 10357; Pelter et al. (1987) *Tetrahedron Lett.* 28: 5213; Grisp (1989) *Synth. Commun.* 19: 307; Yassar et al. (1994) *Adv. Mater.* 6: 660; Lipshutz (1986) *Chem. Rev.* 86: 795; Hou et al. (1998) *Tetrahedron* 54: 1955; and Lee et al. (2000) *J. Am. Chem. Soc.* 122: 4992–4993. For example, shown below is a scheme that depicts a synthetic route. In this scheme, Ar, $R_1$, and $R_2$ are as defined in Summary.

As shown in the above scheme, a furan-containing compound (I) is prepared with a propargylic dithiolacetal compound (II) as a starting material (for synthesis, see, e.g., Lee et al. supra). More specifically, the starting material is reacted with BuLi, followed by addition of an aromatic aldehyde (III) to afford an allenyl carbinol intermediate (IV). The intermediate is then converted to compound (I) by acid treatment (e.g., trifluoroacetic acid).

An asymmetrical furan-containing compound, e.g., having two different $R_2$ groups, can be prepared by partial hydrolysis of an ester group, followed by selective functional group transformations.

The chemicals used in the above-described synthetic routes may include, for example, solvents, reagents, catalysts, protecting group and deprotecting group reagents. The methods described above may also additionally include steps, either before or after the steps described specifically herein, to add or remove suitable protecting groups in order to ultimately allow synthesis of the furan-containing compound described above. In addition, various synthetic steps may be performed in an alternate sequence or order to give a desired compound. Synthetic chemistry transformations and protecting group methodologies (protection and deprotection) useful in synthesizing applicable the claimed compounds are known in the art and include, for example, those described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

A furan-containing compound thus synthesized can be further purified by a method such as column chromatography, high pressure liquid chromatography, recrystallization, or sublimation.

One or more furan-containing compounds can be used as a hole transporting material in an electro-luminescence device.

Typically, an electro-luminescence device is either a two- or a three-layer structured device. A two-layer structured device can include a hole transporting layer and an electron transporting layer, sandwiched between two layers of electrodes. Either the hole transporting layer or the electron transporting layer can function as a luminescent layer, which emits lights (Tang et al. (1989) *J. Appl. Phys.* 65: 3610). Generally, an anode layer, a hole transporting layer, an electron transport layer, and a cathode layer are deposited sequentially in the above order. The anode layer can be formed on a substrate, such as a glass. A three-layer structured device can include a hole transporting layer, a luminescent layer (i.e., light emitting layer), and an electron transporting layer, sandwiched between two layers of electrodes. An anode layer, a hole transporting layer, a luminescent layer, an electron transport layer, and a cathode layer are deposited sequentially in the above order. The luminescent layer can be another hole transporting or another electron transporting layer. Optionally, the electro-luminescence device can include a dopant-containing layer, which can be an electron transporting layer or a luminescent layer.

Each of the above mentioned layers can be made of various materials, as described in, for example, U.S. Pat. No. 5,698,740, Shirota (2000) *Mater. Chem.* 10: 1; Elschner et al. (2000) *Synth. Met.* 111–112: 139; and Groenendaal et al. (2000) *Adv. Mater.* 12: 481. More specifically, a substrate can be made of glass; an anode layer can be a film of a transparent electroconductive material, e.g., indium tin oxide (ITO); an optional hole injecting layer can be made of poly(ethylenedioxy)thiophene and polystyrene sulfonate (PEDT-PSS); a hole transporting layer can be made of 4,4'-bis[N-(1-naphthyl)-N-phenylamino]-biphenyl (NPD); an electron transporting layer can be made of tris(8-oxyquinoline)aluminium (Alq), or dopant (e.g., N,N-dimethylquinacridone DMQA)-containing Alq; and a cathode layer can be made of a metal film, e.g., an alloy of magnesium and silver.

The fabrication of an electro-luminescence device has been described in, for example, Tang & VanSlyke (1987) *Appl. Phys. Lett.* 51: 913; Tang et al. (1989) *J. Appl. Phys.* 65: 3610, or Kido & Lizumi (1997) *Chem. Lett.* 963. More specifically, each layer may be formed by any film forming method such as vacuum deposition. See U.S. Pat. No. 5,698,740.

This invention features a device containing a hole transporting layer that is made of one of the furan-containing compounds described above. Unexpectedly, the furan-containing compound is capable to transport holes at least as efficiently as NPD.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications, including patents, cited herein are hereby incorporated by reference in their entirety.

EXAMPLES $^1$H and $^{13}$C NMR spectra were recorded on a Varian 400-MHz spectrometer. UV-Vis absorption spectra were measured on a Shimadzu UV-1601PC UV-Visible spectrophotometer. Emission spectra were taken on an Aminco-Bowman Series 2 Luminescence spectrometer, and the quantum efficiencies were obtained by standard method using Coumarin 1 (($\Phi_f$=0.99 in ethyl acetate) as reference. FTIR spectra were measured on a Nicolet Magna-IR (series II) spectrophotometer. Cyclic voltammetry experiments were performed with a BAS CV-27 electrochemical analyzer. All measurements were carried out at room temperature with a conventional three-electrode configuration consisting of a platinum working electrode, an auxiliary platinum electrode, and a nonaqueous Ag/AgNO$_3$ (0.01 M in CH$_3$CN) reference electrode. Dichloromethane (CH$_2$Cl$_2$) was used as the solvent, and the supporting electrolyte was 0.1 M Bu$_4$N$^+$PF$_6^-$ in all experiments. $E_{1/2}$ values were determined as $(E_p^a+E_p^c)/2$, where $E_p^a$ and $E_p^c$ are the anodic and cathodic peak potentials, respectively. All potentials are reported with reference to Fc$^+$/Fc external standard. Differential scanning calorimetry (DSC) measurements were obtained on a TA Instrument 2920 thermal analyzer at a heating rate of 10° C./min. TGA measurements were performed on a TA Instrument 2950 TGA thermal analyzer. Elemental analyses were performed on a Perkin-Elmer CHN-2400 II analyzer.

Tetrahydrofuran (THF) was distilled from benzophenone ketyl. CH$_2$Cl$_2$ for reaction and electrochemical measurements was distilled from calcium hydride under nitrogen atmosphere. 1,4-Bisformylbiphenyl (see Colon & Kelsey (1986) *J. Org. Chem.* 51: 2627) and 2-phenyl-2-(2-phenylethynyl)dithiolane (see Lee et al. (2000) *J. Am. Chem. Soc.* 122: 4992) were synthesized according to the literature procedures. NPD, Alq, and DMQA were received from commercial sources and sublimed before use.

Example 1

Synthesis of Furan-containing Compounds

Synthesis of Compound 1

Under nitrogen atmosphere, to a solution of 2-phenyl-2-(2-phenylethynyl)-dithiolane (11.3 g, 40.0 mmol) in THF (200 mL) cooled to −78° C. was added dropwise BuLi (16 mL, 2.5 M in hexane, 150 mmol). The mixture was stirred at −78° C. for 1 h, to which a solution of terephthalaldehyde (2.68 g, 20.0 mmol) in THF (100 mL) was introduced. The mixture was gradually warmed to room temperature. After stirred for an additional 1.5 h, trifluoroacetic acid (3 mL, 39.0 mmol) was added and the mixture was stirred at room temperature for 10 h. It was then quenched with saturated NH$_4$Cl solution, washed with 10% NaHCO$_3$ solution, water, brine, and dried over MgSO$_4$. The mixture was concentrated in vacuo to give Compound 1 (6.0 g, 58%): mp 291–292° C.; $^1$H NMR (400 MHz, CDCl$_3$) δ 6.81 (s, 2H), 7.55 (s, 4H), 7.29 (tt, J=7.2, 1.2 Hz, 2H), 7.35 (tt, J=7.2, 1.2 Hz, 2H), 7.40 (br.t, J=7.2, 4H), 7.41 (br.t, J=7.2 Hz, 4H), 7.48 (dt, J=7.2, 1.2 Hz, 4H), 7.55 (s, 4H); 7.75 (dt, J=7.2, 1.2 Hz, 4H); $^{13}$C NMR (100 MHz, CDCl$_3$) δ 109.7, 123.8, 125.0, 125.8, 127.4, 127.6, 128.71, 128.74, 129.9, 130.4, 134.3, 147.5, 152.6; IR (KBr) 1596, 1513, 1490, 1451, 1151, 954, 759, 692; Anal. Calcd. for C$_{38}$H$_{26}$O$_2$: C, 88.69; H, 5.09. Found: C, 88.63; H, 5.41.

Synthesis of Compound 2

In a manner similar to that described above, 1,4-bis-formylbiphenyl (1.05 g, 5.0 mmol) was allowed to react with the allenyl anion generated from the reaction of 2-phenyl-2-(1-phenylethynyl)-dithiolane (2.82 g, 10 mmol) in THF (100 mL) with BuLi (4 mL, 2.5 M in hexane, 10 mmol). The reaction mixture was then treated with $CF_3CO_2H$ (1.5 mL, 19.5 mmol), followed by usual workup to give Compound 2 (2.5 g, 60%) mp 232–234° C.; $^1H$ NMR (400 MHz, $CDCl_3$) δ 6.82 (s, 2H), 7.28 (tt, J=7.2, 1.2 Hz, 2H), 7.33 (tt, J=7.2, 2.4 Hz, 2H), 7.40 (br.t, J=7.2, 4H), 7.41 (br.t, J=7.2, 4H), 7.49 (dt, J=7.2, 1.2 Hz, 4H), 7.54 (dt, J=8.8, 1.6 Hz, 4H), 7.66 (dt, J=8.8, 1.6 Hz, 4H), 7.76 (dt, J=7.2, 1.6 Hz, 4H); $^{13}C$ NMR (400 MHz, $CDCl_3$) δ 109.7, 123.9, 124.9, 126.4, 126.8, 127.4, 127.6, 128.7, 128.8, 130.1, 130.5, 134.3, 139.3, 147.6, 152.7; IR (KBr) 1596, 1505, 1490, 1451, 1151, 823, 758, 701; Anal. Calcd. for $C_{38}H_{26}O_2$: C, 89.46; H, 5.12. Found: C, 89.41; H, 4.95.

Synthesis of Compound 3

In a manner similar to that described above, the reaction of 2-(hex-1-yn-1-yl)-2-phenyldithiolane (520 mg, 2.0 mmol) in THF (10 mL) with n-BuLi (0.8 mL, 2.5 M in hexane, 2 mmol) afforded the corresponding allenyl anion. The reaction mixture was then treated sequentially with 1,4-bisformylbiphenyl (210 mg, 1.0 mmol) and with $CF_3CO_2H$ (0.4 mL, 5.2 mmol), followed by usual workup to afford Compound 3 (187 mg, 34%): mp 152–153° C.; $^1H$ NMR (400 MHz, $CDCl_3$) δ 0.99 (t, J=7.3 Hz, 6H), 1.48 (sext, J=7.3, 4H), 1.72 (tt, J=7.6, 7.3 Hz, 4H), 2.75 (t, J=7.6, 4H), 6.69 (s, 2H), 7.27 (t, J=7.9, 2H), 7.41(t, J=7.9, 4H), 7.73 (d, J=8.6, 2H), 7.75 (t, J=7.9, 4H), 7.80 (d, J=8.6, 4H); $^{13}C$ NMR (100 MHz, $CDCl_3$) δ 14.0, 22.7, 25.9, 32.1, 109.4, 123.7, 124.5, 125.8, 126.9, 127.2, 128.7, 130.76, 130.78, 138.7, 147.6, 152; IR (neat,): 3034, 2960, 2931, 2873, 2858, 1613, 1594, 1577, 1534, 1493, 1474, 1374, 1276, 1191, 1115, 1073, 1003, 931, 910, 824, 798, 761, 722, 691, 667, 490 $cm^{-1}$; Anal. Calcd. for $C_{40}H_{38}O_2$: C, 87.24; H, 6.95. Found: C, 87.16; H, 7.27.

The photophysical properties as well as thermochemistry data are summarized in Table 1. As revealed by thermogravimetric analysis (TGA) experiments, Compounds 1, 2, and 3 were thermally stable, neither decomposition nor vaporization being observed at 300° C. No spectroscopic changes (NMR, UV-Vis, and fluorescence) were observed when the compounds were treated under nitrogen atmosphere at 200° C. for 24 h. Glass transition temperatures ($T_g$) of Compounds 1, 2, and 3 were 88, 96, and 23° C., respectively.

TABLE 1

Physical Properties of Compounds 1, 2, and 3, NPD, and Alq

| Compound | $T_g^a$ (° C.) | $T_c^a$ (° C.) | $T_d^b$ (° C.) | $\lambda_{max}$ (nm) | $\lambda_{em}$ (nm) | $\Phi_f^c$ | $E_{ox}^{1/2}$ vs. $Fc^d$ | HOMO (eV) | LUMO (eV) |
|---|---|---|---|---|---|---|---|---|---|
| Compound 1 | 88 | 98 | 308 | 245, 383(253, 395) | 439, 457(461, 480) | 0.91 | 548 | 5.35 | 2.45 |
| Compound 2 | 96 | $na^e$ | 434 | 244, 374(245, 375) | 436, 459(450, 478) | 0.92 | 645 | 5.45 | 2.51 |
| Compound 3 | 23 | 73 | 339 | 240, 368(238, 371) | 424, 448(440, 464) | 0.95 | 550 | 5.35 | 2.34 |
| NPD | 102 | 179 | 382 | 273, 342(345) | 430(465) | 0.16 | 297 | 5.10 | 2.02 |
| Alq | na | na | na | 262, 388(262, 395) | 503(507) | na | na | 5.86 | 3.05 |

$^a$Obtained from differential scanning calorimetry (DSC) measurements;
$^b$Decomposition temperature at 5% weight loss measured by TGA under $N_2$ atmosphere;
$^c$Quantum yield measured in $CHCl_3$ relative to Coumarin 1;
$^d$Measured in $CH_2Cl_2$, all oxidation potentials are relative to ferrocene/ferrocenium half cell.
$^e$na: not available.

As shown in Table 1, Compounds 1, 2, and 3 exhibited blue emission with quantum yields in the range of 0.91–0.95. They also showed reversible redox waves as examined by cyclic voltammetry. The highest occupied molecular orbital (HOMO) energy levels of these compound were calculated based on the value of –4.8 eV for ferrocene with respect to zero vacuum level. See, e.g., Thelakkat & Schmidt (1998) *Adv. Mater.* 10: 219. The lowest unoccupied molecular orbital (LUMO) energy levels were thus obtained by substracting the corresponding energy gap estimated from the absorption onset wavelength. See, e.g., Miyame et al. (1995) *J. Chem. Phys.* 103: 2738. The HOMO and LUMO levels for NPD are also listed for comparison. It is noteworthy that the HOMO and LUMO energy levels for Compounds, 1, 2, and 3 were slightly higher than that of NPD and fit very well with the frontier orbital energy for Alq.

Example 2

Fabrication of Devices

Nine devices were fabricated as follows:

A device on the glass substrate had the typical structure of multiple organic layers sandwiched between ITO anode and Mg:Ag(80 nm)/Ag(150 nm) or LiF(0.5 nm)/Al(150 nm) bilayer cathode. The device also included a hole injecting layer made of PEDT:PSS (Bayer Corp.), a hole transporting layer made of NPD or furan compounds, and an electron transporting layer/light emitting layer made of Alq. The PEDT:PSS layer was prepared by spin coating. All the other organic materials were deposited at a rate of 0.2–0.3 nm/s by thermal evaporation at ~$10^{-6}$ Torr. Unless otherwise specified, the thicknesses of the hole injecting layer, the hole transporting layer, and the electron transporting layer were 30, 40, and 60 nm, respectively. DMQA was used as a dopant in the electron transporting layer. The current-voltage-brightness (I-V-L) characterization of each device was carried out by an Agilent 4155B semiconductor parameter analyzer and calibrated with silicon photodetectors.

The fabricated devices were tested. The results were outlined in Table 2.

TABLE 2

Electroluminescence Data for Nine Devices.

| Device Configuration[a] | $\lambda_{EL}$[b] | $V_{on}$[c] | $V_{20}$[d] | $B_{20}$[e] | $V_{max}$[f] | $B_{max}$[g] | $\eta_{max}$[h] | Lum Eff[i] 20 mA/cm² | Peak |
|---|---|---|---|---|---|---|---|---|---|
| 1 ITO/PEDT:PSS/Compound 1/Mg:Ag/Ag[j] | 476 | 4.3 | 8.3 | 7 | 11.5 | 260 | 0.23 | 0.1 | 0.3 |
| 2 ITO/PEDT:PSS/Compound 1/Alq/Mg:Ag/Ag | 530 | 2.5 | 8.3 | 770 | 12.0 | 18,600 | 1.32 | 1.5 | 1.6 |
| 3 ITO/PEDT:PSS/NPD/Alq/Mg:Ag/Ag | 532 | 2.5 | 9.0 | 736 | 13.0 | 16,650 | 1.35 | 1.3 | 1.4 |
| 4 ITO/PEDT:PSS/Compound 2/Alq/Mg:Ag/Ag | 540 | 2.5 | 11.5 | 747 | 16.0 | 16,100 | 1.33 | 1.0 | 1.1 |
| 5 ITO/PEDT:PSS/Compound 3/Alq/Mg:Ag/Ag | 538 | 2.5 | 9.6 | 1,050 | 12.5 | 9,000 | 1.75 | 2.1 | 2.2 |
| 6 ITO/PEDT:PSS/Compound 1/Alq/LiF/Al | 535 | 2.0 | 6.8 | 869 | 11.5 | 30,400 | 1.48 | 2.6 | 3.6 |
| 7 ITO/PEDT:PSS/NPD/Alq/LiF/Al | 537 | 2.0 | 6.8 | 711 | 12.0 | 30,800 | 1.29 | 2.1 | 2.7 |
| 8 ITO/PEDT:PSS/Compound 1/Alq:DMQA (0.5%)/Alq/LiF/Al[k] | 542, 578 | 2.0 | 7.9 | 2,050 | 18.0 | 182,800 | 2.78 | 6.9 | 10.1 |
| 9 ITO/PEDT:PSS/NPD/Alq:DMQA (0.5%)/Alq/LiF/Al[k] | 542, 578 | 2.0 | 8.4 | 1,970 | 19.5 | 180,400 | 2.67 | 6.2 | 9.3 |

[a]Thickness: PEDT:PSS (30 nm), hole transporting layer (40 nm), Alq (60 nm), unless otherwise specified.
[b]EL maximum (nm);
[c]Turn-on voltage (V) at which emission starts to be detectable;
[d]Voltage (V) taken at a current density of 20 mA/cm²;
[e]Brightness (cd/m²) taken at a current density of 20 mA/cm²;
[f]Voltage (V) at the maximum brightness;
[g]Maximum brightness (cd/m²);
[h]Maximum external quantum efficiency;
[i]Luminous efficiency (lm/W) taken at 20 mA/cm²;
[j]The thickness of the layer containing Compound 1 is 120 nm;
[k]Alq:DMQA (20 nm), Alq (40 nm).

Device 1, containing ITO/PEDT:PSS/Compound 1 (120 nm)/Mg:Ag (800 nm)/Ag (150 nm), exhibited a blue emission at 476 nm and tolerated very high current density of 2500 mA/cm² at 12.5 V. The external quantum efficiency of 0.23% and the brightness of 260 cd/m² for this device were obtained.

In device 2, the double layer device with the configuration of ITO/PEDT:PSS/Compound 1 (40 nm)/Alq (60 nm)/Mg:Ag (800 nm)/Ag (150 nm) was fabricated. Device 3 had similar configuration using NPD as the hole transporting material. Both devices produced the typical emission of Alq at 530 nm. The two devices had similar turn-on voltage and external quantum efficiency, but unexpectedly, device 2 has a higher maximal brightness (18,600 cd/m²) than that of device 3 (16,650 cd/m²). When Compound 2 (device 4) and Compound 3 (device 5) were employed as the hole transporting materials, the maximal brightness reached 16,000 and 9,000 cd/m², respectively.

LiF/Al has been used as a cathode in an OLED device. See, e.g., Huang et al. (1997) *Appl. Phys. Lett.* 70: 152; and Jabbour et al. (1997) *Appl. Phys. Lett.* 71: 1762. Two devices were fabricated with the configuration of ITO/PEDT:PSS/hole transporting layer (40 nm)/Alq (60 nm)/LiF (0.5 nm)/Al (150 nm), wherein the hole transporting layer was made of either Compound 1 (device 6) or NPD (device 7). Both devices had a turn-on voltage (including the control device) of 2.0 V. In addition, the operating voltage at 20 mA/cm² was 6.8 V. The external quantum efficiency of device 6 was 1.48% and the maximum brightness for both devices 6 and 7 was about 3×10⁴ cd/m².

DMQA can serve as an effective emissive dopant for Alq. See, e.g., Shi & Tang (1997) *App. Phyl. Lett.* 70: 1665. To obtain a device with the optimized configuration, multilayer devices ITO/PEDT:PSS/hole transporting layer (40 nm)/Alq:DMQA (20 nm)/Alq (40 nm)/LiF (0.5 nm)/Al (150 nm) were fabricated, wherein the hole transporting layer was made of Compound 1 (device 8) or NPD (device 9). Various DMQA concentrations were used and the emissive maximum was 542 nm, with a shoulder at 578 nm. The optimal DMQA concentration in Alq was found to be 0.5%, providing an external quantum efficiency of 2.78% and a maximum luminance of 182,800 cd/m² at 18 V for device 8. The external quantum efficiency and the maximal luminance for device 9 were 2.67% and 180,200 cd/m² at 19.5 V, respectively.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Accordingly, other embodiments are also within the scope of the following claims.

What is claimed is:
1. A compound of formula (I):

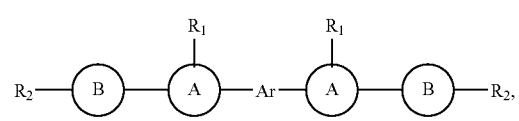

wherein
Ar is aryl, heteroaryl, or oligoaryl;
A is furyl;
B is aryl or heteroaryl;

R₁ is alkenyl, alkynyl, aryl, heteroaryl, cyclyl, heterocyclyl, or oligoaryl; and R₂ is hydrogen, alkyl, alkenyl, alkynyl, aryl, heteroaryl, cyclyl, or heterocyclyl.

2. The compound of claim 1, wherein A is furyl substituted at positions 2 and 5.

3. The compound of claim 1, wherein B is aryl.

4. The compound of claim 3, wherein B is phenyl.

5. The compound of claim 4, wherein R₂ is hydrogen.

6. The compound of claim 1, wherein Ar is aryl.

7. The compound of claim 6, wherein Ar is phenyl.

8. The compound of claim 7, wherein A is furyl substituted at positions 2 and 5.

9. The compound of claim 8, wherein B is aryl.

10. The compound of claim 9, wherein B is phenyl.

11. The compound of claim 10, wherein R₂ is hydrogen.

12. The compound of claim 11, wherein R₁ is phenyl, and substituted at position 3 of furyl.

13. The compound of claim 1, wherein Ar is oligoaryl.

14. The compound of claim 13, wherein Ar is biphenyl.

15. The compound of claim 14, wherein A is furyl substituted at positions 2 and 5.

16. The compound of claim 15, wherein B is aryl.

17. The compound of claim 16, wherein B is phenyl.

18. The compound of claim 17, wherein R₂ is hydrogen.

19. The compound of claim 18, wherein R₁ is phenyl, and substituted at position 3 of furyl.

20. An electro-luminescence device, comprising:

an anode layer, a hole transporting layer, an electron transporting layer, and a cathode layer, wherein the anode layer, the hole transporting layer, the electron transporting layer, and the cathode layer are disposed in the above order; and the hole transporting layer includes a compound of formula (I):

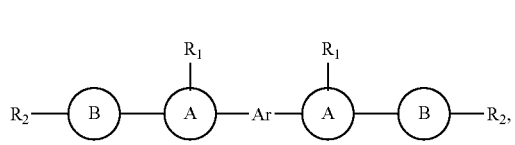

in which

Ar is aryl, heteroaryl, or oligoaryl;

A is furyl;

B is aryl or heteroaryl;

R₁ is alkenyl, alkynyl, aryl, heteroaryl, cyclyl, heterocyclyl, or oligoaryl; and R₂ is hydrogen, alkyl, alkenyl, alkynyl, aryl, heteroaryl, cyclyl, or heterocyclyl.

21. The device of claim 20, wherein A is furyl substituted at positions 2 and 5.

22. The device of claim 20, wherein B is aryl.

23. The device of claim 22, wherein B is phenyl.

24. The device of claim 23, wherein R₂ is hydrogen.

25. The device of claim 20, wherein Ar is aryl.

26. The device of claim 25, wherein Ar is phenyl.

27. The device of claim 26, wherein A is furyl substituted at positions 2 and 5.

28. The device of claim 27, wherein B is aryl.

29. The device of claim 28, wherein B is phenyl.

30. The device of claim 29, wherein R₂ is hydrogen.

31. The device of claim 30, wherein R₁ is phenyl, and substituted at position 3 of furyl.

32. The device of claim 20, wherein Ar is oligoaryl.

33. The device of claim 32, wherein Ar is biphenyl.

34. The device of claim 33, wherein A is furyl substituted at positions 2 and 5.

35. The device of claim 34, wherein B is aryl.

36. The device of claim 35, wherein B is phenyl.

37. The device of claim 36, wherein R₂ is hydrogen.

38. The device of claim 37, wherein R₁ is phenyl, and substituted at position 3 of furyl.

* * * * *

UNITED STATES PATENT AND TRADEMARK OFFICE
CERTIFICATE OF CORRECTION

PATENT NO. : 7,128,983 B2
APPLICATION NO. : 10/643041
DATED : October 31, 2006
INVENTOR(S) : Tien-yau Luh et al.

It is certified that error appears in the above-identified patent and that said Letters Patent is hereby corrected as shown below:

Title page, Item (75), please delete "Cheih-Wei Chen" and insert --Chieh-Wei Chen--.

Signed and Sealed this
Second Day of October, 2012

David J. Kappos
*Director of the United States Patent and Trademark Office*